United States Patent [19]

Yamada et al.

[11] Patent Number: 4,980,278

[45] Date of Patent: Dec. 25, 1990

[54] METHOD OF EFFECTING IMMUNOLOGICAL ANALYSIS AND APPARATUS FOR CARRYING OUT THE SAME

[75] Inventors: Takashi Yamada, Sagamihara; Nobutaka Kaneko, Hachioji; Takashi Tabara, Kokubunji; Takeo Takahashi, Hachioji, all of Japan

[73] Assignee: Olympus Optical Co., Ltd., Tokyo, Japan

[21] Appl. No.: 342,589

[22] Filed: Apr. 24, 1989

Related U.S. Application Data

[63] Continuation of Ser. No. 866,912, May 27, 1986, abandoned.

[30] Foreign Application Priority Data

May 28, 1985 [JP] Japan .................................. 60-113055
May 28, 1985 [JP] Japan .................................. 60-113052

[51] Int. Cl.$^5$ ..................... G01N 33/53; G01N 31/00; G01N 33/48; G01N 33/552
[52] U.S. Cl. ........................................... 435/7; 422/57; 422/82.05; 422/82.06; 422/82.07; 424/11; 350/96.3; 356/39; 356/221; 356/436; 436/501; 436/520; 436/527; 436/536; 436/538; 436/165; 436/805; 436/807; 436/810
[58] Field of Search ................ 435/7, 288; 436/520, 436/536, 538, 540, 541, 807, 810, 501, 527, 165, 805; 422/57, 68, 136, 163, 85.05, 85.06, 85.07; 424/11; 350/96.3; 356/39, 221, 436

[56] References Cited

U.S. PATENT DOCUMENTS

| | | | |
|---|---|---|---|
| 4,050,895 | 9/1977 | Hardy et al. | 424/12 |
| 4,272,245 | 6/1981 | Diamond et al. | 422/61 |
| 4,279,992 | 7/1981 | Boguslaski et al. | 435/7 |
| 4,490,473 | 12/1984 | Brunhouse | 436/518 |
| 4,582,809 | 4/1986 | Block et al. | 422/68 |
| 4,647,153 | 3/1987 | Utsumi et al. | 350/96.26 |
| 4,647,544 | 3/1987 | Nicoli et al. | 436/518 |
| 4,657,869 | 4/1987 | Richards et al. | 435/287 |
| 4,737,343 | 4/1988 | Hirschfield | 422/63 |

FOREIGN PATENT DOCUMENTS

0100349 6/1982 Japan .
0131062 8/1982 Japan .

Primary Examiner—Esther L. Kepplinger
Assistant Examiner—Florina B. Hoffer
Attorney, Agent, or Firm—Parkhurst, Wendel & Rossi

[57] ABSTRACT

A method for analyzing antigen or antibody contained in a sample by introducing a first end surface of at least one measuring light guide member and a second end surface of at least one reference light guide member in the sample. Each of said measuring and reference light guide members being coated with a protection layer except for said first and second end surfaces and an other end surface of respect light guides. Only on said first end surface of the measuring light guide member being fixed an antigen or antibody which is specifically reactive with the antigen or antibody contained in the sample to effect an antigen-antibody reaction. Photoelectrically detecting optical properties of said first and second end surfaces of the measuring and reference light guide members, respectively, by transmitting light through the meauring and reference light guide members to derive detection signals as a measure of antigen or antibody in the sample. Further, when first and second measuring light guide members having A-type antibody and B-type antibody fixed onto one end surfaces thereof are used, a blood type of a blood sample can be determined by detecting the optical condition of the one end surfaces of the first and second measuring light guide members.

55 Claims, 9 Drawing Sheets

METHOD OF EFFECTING IMMUNOLOGICAL ANALYSIS AND APPARATUS FOR CARRYING OUT THE SAME

This is a continuation of application Ser. No. 06/866,912 filed May 27, 1986, now abandoned.

BACKGROUND OF THE INVENTION

Field of the Invention and Related Art Statement

The present invention relates to a method of effecting an immunological analysis.

Due to recent progress in the medical field it has become possible to analyze very small amounts of biological substances, and this contributes to early stage diagnosis for various diseases. For instance, malignant tumors can be diagnosed at an early stage by measuring alpha-fetoprotein and carcinoembryonic antigen. Further, immunological diseases can be diagnosed by measuring abnormal secretion of hormones such as insulin and thyroxine and immunoglobulin. Moreover, it has also become possible to effect monitoring during the course of medical treatment. Further analysis for low molecular hapten (incomplete antigen) such as medicines, contributes to plan a dose schedule of medicines.

Most of these biological substances have been analyzed by an immunological method utilizing the antigen-antibody reaction. There have been proposed various immunological analyzing methods. For instance, antigen or antibody is fixed on fine particles made of glass or synthetic resin and is reacted with a sample antibody or antigen, while labeling antibody or antigen labeled with a highly sensitive marker such as radio isotope, fluorescent substance, luminescent substance and enzyme is used to produce antigen-antibody complex. Then the antigen-antibody complex is detected to quantify the sample antigen or antibody.

Figure 1:
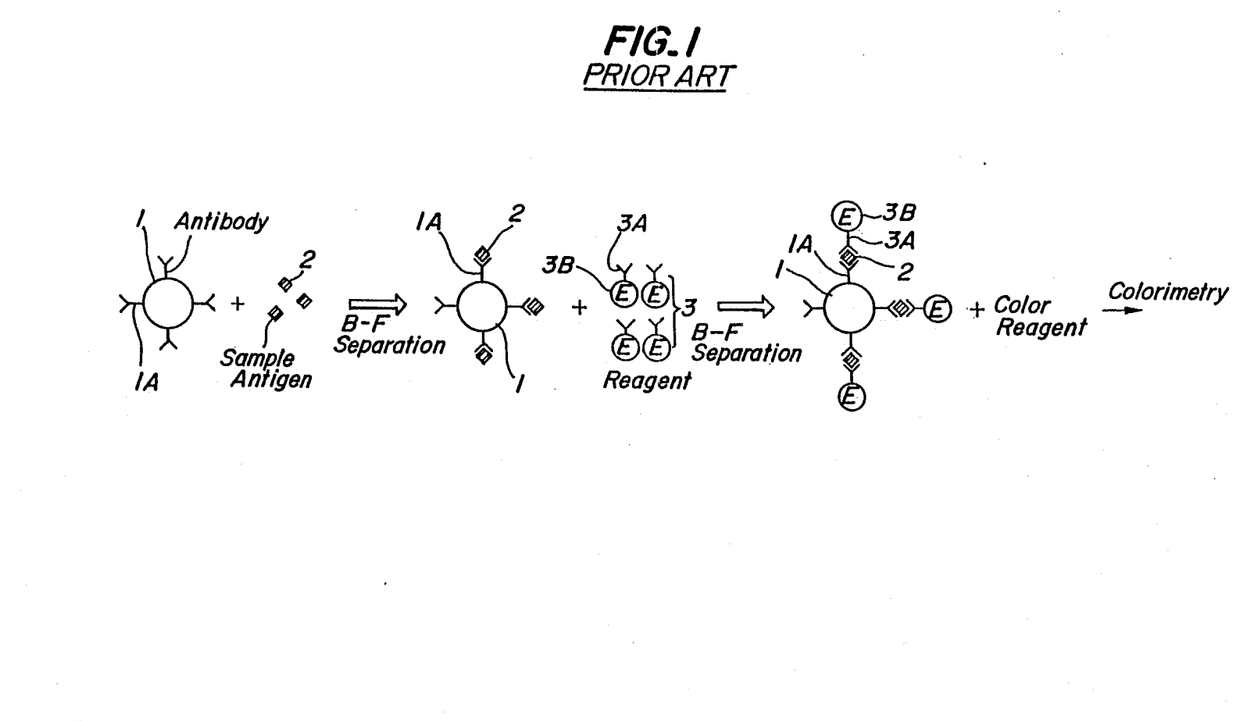
FIG. 1 is a schematic view showing a reaction process of the known immunological analyzing method.

FIG. 1 shows a reaction process of known enzyme immunological analysis utilizing an enzyme labeling reagent. On an outer surface of an insoluble carrier 1 there is fixed antibody 1A which is specifically reacted with antigen contained in a sample to be analyzed. If sample antibody instead of antigen is to be measured, antigen which is specifically reacted with the sample antibody has to be fixed onto the insoluble carrier 1. At first, the antibody 1A on the carrier 1 is reacted with antigen 2 contained in the sample. Then free antigen which has not been bound with the antibody 1A on the carrier 1 is separated from antigen 1A bound on the carrier 1 by means of washing. This separating process is generally called B-F separation. After that, the carrier 1 is reacted with a labeling reagent 3 comprising antibody 3A labeled with enzyme 3B, said antibody 3A being specifically reacted with the sample antigen 2. Next, the B-F separation is carried out again to separate free labeling reagent from labeling reagent bound with the sample antigen 2 reacted with the antibody 1A fixed on the carrier 1. Further, a color reagent is added to effect a color reaction under the existence of the enzyme 3B of the labeling reagent 3. Finally the reaction liquid is colorimetered to detect an enzyme activity. In this manner the sample substance 2 is quantified at a high sensitivity. The above mentioned immunological analyzing method has become widely practiced.

In the known immunological analyzing method using a labeling reagent containing antibody or antigen, after the antibody or antigen fixed on the carrier has been reacted with the sample antigen or antibody, the first B-F separation is performed, and then after the sample antigen or antibody has been reacted with the labeling reagent, the second B-F separation is carried out. Therefore, the analysis requires a larger number of steps and the analyzing process is liable to be complicated. Moreover, it is necessary to use various kinds of reagents and thus the running cost becomes expensive. It should be noted that an analyzer for effecting the known analysis becomes also complicated and expensive.

Further, since the substance to be analyzed is detected indirectly by using the labeling reagent as intermediate substance, the analysis is liable to be affected by slight change in external condition during the analyzing process. For instance, if the washing process is not carried out correctly, there might be produced measuring errors.

The immunological analysis has been also used to identify or determine a blood type. For instance, in German Patent No. 3,246,873, there is disclosed a method of determining the blood type by photoelectrically detecting a particle agglutination pattern. In this known method, blood cells are first separated by centrifuge, and then separated blood cells are dispersed in a saline solution to form a blood cell solution having a concentration of 2 to 5%. The blood cell solution is delivered into a reaction vessel having a conical bottom and a given antiserum is delivered into the reaction vessel. A particle pattern formed on the conical bottom is uniformly illuminated and is photoelectrically detected. A photoelectric output signal is processed to judge agglutinated or non-agglutinated particle pattern to determine the blood type.

In the above mentioned known blood type determining method, there are required various processes such as the centrifugal separation of blood cells, preparation of the blood cell suspension and the delivery of the antiserum. Therefore, the analyzing process is very cumbersome. Moreover, in order to form the particle pattern the reaction vessel has to remain still for a long time period. Further, in order to detect the particle pattern, there must be arranged correctly a light source, imaging lens, a plurality of light receiving elements, etc. Thus, the whole analyzing apparatus is liable to be large in size, complicated in construction and expensive in cost.

SUMMARY OF THE INVENTION

The present invention has for its object to provide a novel and useful method of effecting an immunological analysis, in which substances contained in samples can be directly analyzed in a simple and accurate manner.

It is another object of the invention to provide a method of effecting an immunological analysis, which can be performed by a simple and small apparatus.

It is still another object of the invention to provide a method of determining a blood type by utilizing the immunological reaction in a simple and accurate manner.

It is still another object of the invention to provide a method of determining the ABO blood type by means of a simple and small apparatus.

According to the invention, a method of quantifying antigen or antibody contained in a sample in an immunological manner comprises the steps of:

introducing at least one end surface of a light guide member into a sample, on said one end surface of the light guide member being fixed substance which is specifically reactive with substance in the sample to be analyzed;

effecting an antigen-antibody reaction between the substance fixed to the light guide member and the substance in the sample; and photoelectrically detecting optical condition of the one end surface of the light guide member by transmitting light through the light guide member to detect the substance contained in the sample.

In a preferred embodiment of the analyzing method according to the invention, use is made of the light guide member formed by an optical fiber, and antibody which is specifically reactive with antigen to be analyzed in a sample is fixed to one end surface of the optical fiber. The one end of the optical fiber is immersed into the sample liquid to effect the antigen-antibody reaction. Then optical condition of the one end surface of the optical fiber is photoelectrically detected by making a light beam incident upon the other end of the optical fiber. Then the light beam propagates within the optical fiber and is projected upon the one end surface of the optical fiber. Optical property of the one end surface is changed in accordance with the antigen in the sample bound with the fixed antibody. Therefore, by detecting light transmitted through the first end surface of the optical fiber it is possible to analyze the antigen contained in the sample. That is to say, when an amount of the antigen contained in the sample is small, only a small amount of the antigen is bound on the one end surface of the optical fiber, so that a large amount of light is transmitted through the one end surface. Therefore, by detecting an amount of light transmitted through the optical fiber, it is possible to quantify a total amount of the antigen contained in the sample.

DESCRIPTION OF THE PREFERRED EMBODIMENTS

Figure 2:
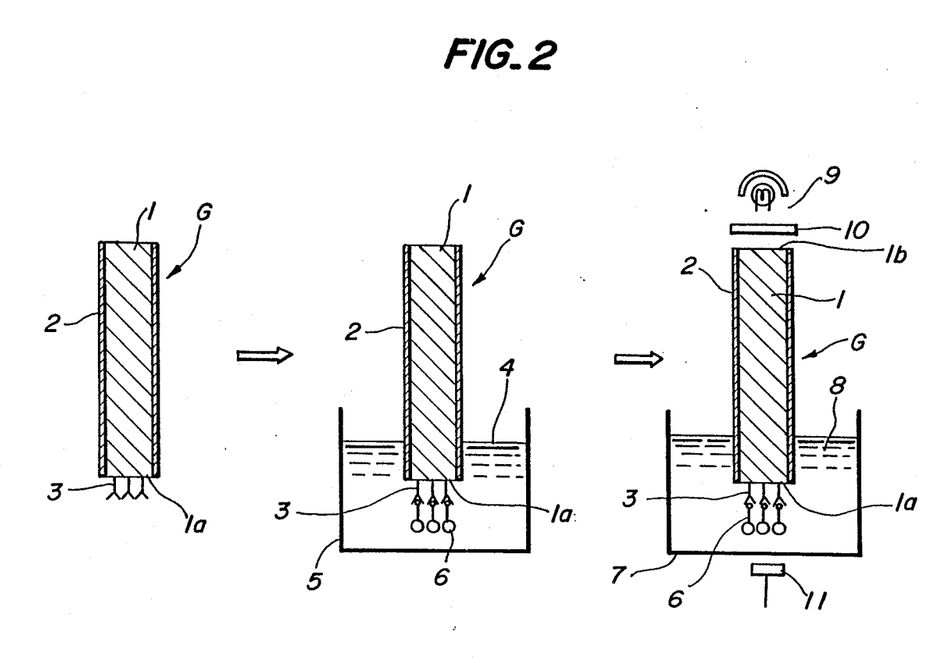
FIG. 2 is a schematic view illustrating an analyzing process in an embodiment of the analyzing method according to the invention.

FIG. 2 is a schematic view illustrating successive steps of an embodiment of the analyzing method according to the invention. In this embodiment, blood cell antigen (i.e., antigen bound on the surface of the blood cell) contained in a blood sample is to be quantified. A light guide member G consisting of a rod 1 made of transparent glass or plastics and is coated with a protection layer 2 made of light shielding material. Onto one end surface 1a of the rod 1 is fixed antibody 3 which is specifically reactive with the blood cell antigen in the blood sample. The light guide member G having the antibody 3 fixed onto the end surface 1a thereof serves as a sensor. The light guide member G may be composed of a single optical fiber, an optical fiber bundle or any type of optical wave guide which can propagate light from one end to the other end.

A blood cell (i.e., sample) 4 to be analyzed is contained in a vessel 5 and the end portion of the light guide member G on which the antibody 3 is fixed is immersed into the blood sample 4 to effect the immunological reaction between the antibody 3 and the antigen in the sample, so that blood cells 6 are bound on the end surface 1a of the rod 1. After the reaction, the light guide member G is removed from the blood sample 4 and is then immersed into a saline solution 8 contained in a vessel 7 made of transparent material. A light source 9 and a filter 10 are arranged above the other end surface 1b of the light guide member G and a light receiving element 11 is provided below the vessel 7. Transmission characteristics of the filter 10 correspond to an absorption peak of the blood cell 6 to be detected. Light emitted from the light source 9 is made incident upon the end surface 1b of the light guide rod 1 via the filter 10 and propagates within the rod toward its end surface 1a on which the blood cell antigen 6 has been bound. The light is absorbed by the blood cells and an amount of the absorbed light is proportional to an amount of the blood cells 6 bound on the end surface 1a of the light guide rod 1. Therefore, an output signal from the light receiving element 11 which receives light emanating from the end surface 1a is proportional to an amount of the blood cells 6 bound on the end surface 1a and thus a total amount of blood cells contained in the blood sample 4. In this manner, it is possible to quantify directly the blood cells contained in the blood sample 4.

In the above embodiment, the end portion of the light guide member G is immersed into the saline solution 8 so as to clean the end portion, and the photoelectric measurement is performed while the end portion of the light guide member G is remained in the saline solution 8. However, according to the invention it is also possible to effect the photoelectric measurement in the air. Further, the photoelectric measurement may be carried out in the reaction vessel 5. Moreover, the position of the light source 9 and light receiving element 11 may be reversed. Then, light emitted from the light source is made incident upon the end surface 1a of the rod 1, light modulated or attenuated by the blood cells 6 bound on the end surface 1a propagates within the rod 1 up to the end surface 1b, and the light emanating from the end surface 1b is made incident upon the light receiving element.

Figure 3:
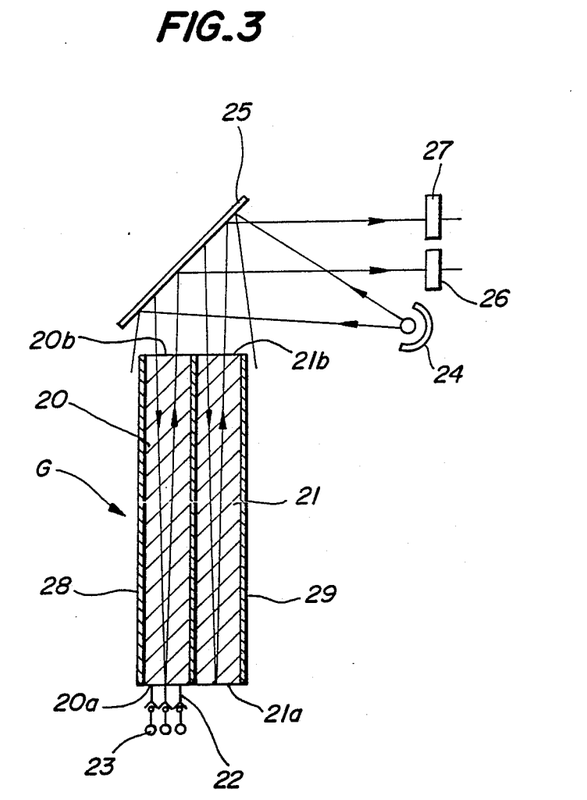
FIG. 3 is a schematic view illustrating another embodiment of the analyzing method according to the invention.

FIG. 3 is a schematic view showing another embodiment of the method according to the invention. In the present embodiment a light guide member G comprises a measuring light guide rod 20 and a reference light guide rod 21 which are integrally coupled with each other and are arranged side by side. On an end surface 20a of the rod 20 is fixed antibody 22 which is specifically reactive with blood cells 23 to be analyzed. There are further arranged a light source 24, a reflection mirror 25 and a pair of light receiving elements 26 and 27. The rods 20 and 21 are coated with protection layers 28 and 29, respectively.

Light emitted from the light source 24 and reflected by the mirror is made incident upon other end surfaces 20b and 21b of the rods 20 and 21 and propagates within the rods up to their end surfaces 20a and 21a. Since the blood cells 23 are bound on the end surface 20a of the rod 20, the light is reflected at the end surface 20a. An amount of light reflected at the end surface 20a is proportional to an amount of the blood cells 23 bound with the antibody 22 fixed onto the end surface 20a. Contrary to this, since no blood cell is bound on the end surface 21a of the reference rod 21, light impinging upon this end surface 21a is almost transmitted therethrough and only a very small amount of light is reflected thereby. Light beams reflected at the end surfaces 20a and 21a of the rods 20 and 21 are transmitted through the rods 20 and 21, respectively, reflected by the mirror 25 and are made incident upon the light receiving elements 26 and 27, respectively. By comparing output signals generated from the light receiving elements 26 and 27, it is possible to measure an amount of blood cells contained in a blood sample. In the present embodiment, since there is provided a reference channel comprising the reference light guide rod 21 and light receiving element 27, error components can be effectively removed, so that the analyzing accuracy can be improved.

Figure 4:
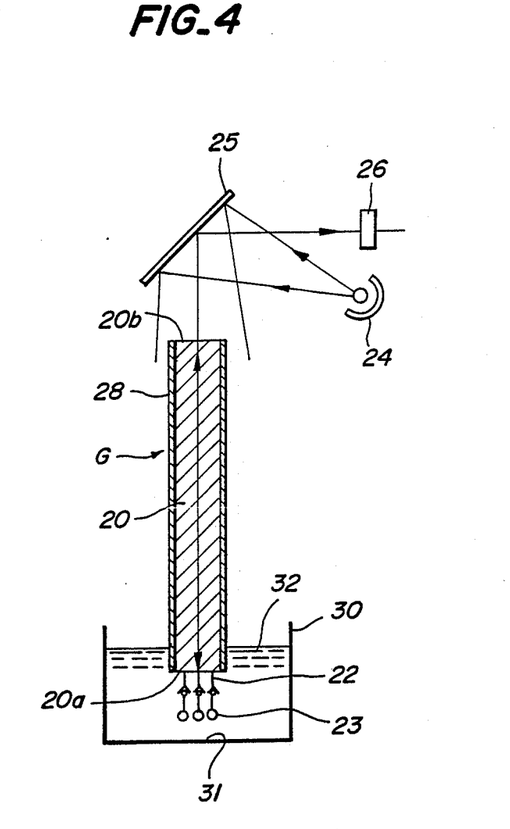
FIG. 4 is a schematic view showing another embodiment of the analyzing method according to the invention.

FIG. 4 is a schematic view depicting a modification of the embodiment shown in FIG. 3. In the present embodiment, after the antigen-antibody reaction the light guide member G comprising a light guide rod 20 having a protection layer 28 is immersed into a saline solution 32 contained in a vessel 30 having a mirror surface 31 formed in a bottom wall.

Light emitted from a light source 24 is reflected by a reflection mirror 25 and is made incident upon an end surface 20b of the rod 20. The light propagates within the rod 20 and is partially absorbed by the blood cells 23 bound with the antibody 22 fixed onto the end surface 20a of the rod 20. Light transmitted through the end surface 20a is reflected by the mirror surface 31 formed in the vessel 30 and is made incident again upon the end surface 20a. The light is partially absorbed again by the blood cells 23 and propagates within the rod 20 and emanates from the end surface 20b of the rod 20. The light is then reflected by the mirror 25 and is made incident upon the light receiving element 26. In the present embodiment, since the light is transmitted through the blood cells 23 twice, S/N of an output signal from the light receiving element 26 is increased and the analysis accuracy is improved.

Figure 5:
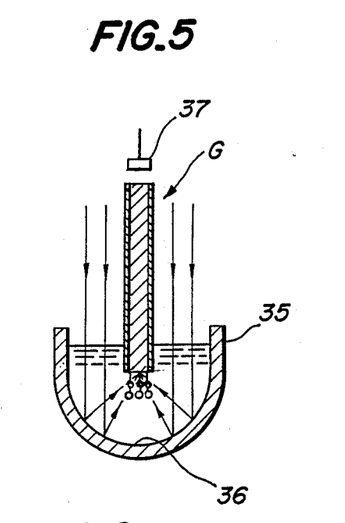
FIGS. 5 and 6 are schematic views depicting still further embodiments of the analyzing method according to the invention in which a spherical vessel is used.

FIG. 5 is a schematic view showing another embodiment of the analyzing method according to the invention. In this embodiment, use is made of a vessel 35 having a spherical bottom on which a mirror surface 36 is formed. After blood cells in the sample have been bound on the end surface of the light guide member G, the light guide member G is placed in such a position that the end surface of the light guide member G situates at a center of the spherical bottom of the vessel 35. When a parallel light flux is projected onto the vessel 35, light rays reflected by the mirror surface 36 formed in the round bottom of the vessel 35 are collected at the end surface of the light guide member G. Light rays introduced into the light guide member G is made incident upon a light receiving element 37.

Figure 6:
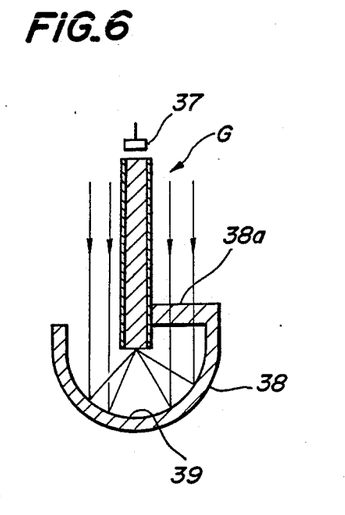

FIG. 6 shows a modified embodiment of the vessel shown in FIG. 5. In the present embodiment, a light guide member G is fixed to an arm 38a of a vessel 38 having a spherical bottom and a mirror surface 39 is formed on an inner surface of the bottom. The assembly of the light guide member G and vessel 38 is immersed in a blood sample to effect the antigen-antibody reaction and then the condition of the end surface of the light guide member G is photoelectrically detected by means of a light receiving element 37, while the assembly remains in the blood sample. It is possible to perform the measurement after the assembly is removed from the reaction vessel and the blood sample is replaced by clear liquid such as water and saline solution.

Figure 7:
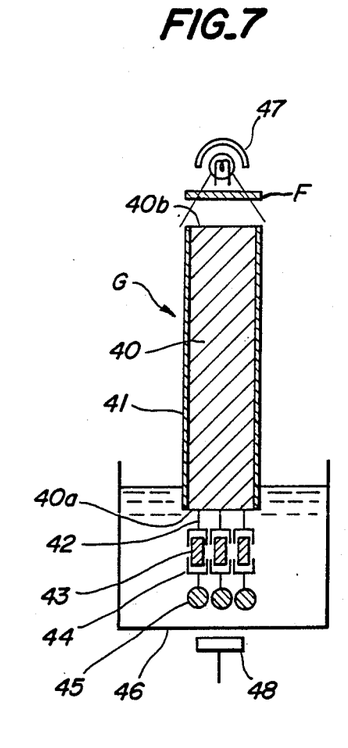
FIGS. 7 and 8 are schematic views showing other embodiments of the analyzing method according to the invention in which a labeling reagent is used.

FIG. 7 is a schematic view illustrating another embodiment of the analyzing method according to the invention. In the present embodiment, a light guide member G comprises a light guide rod 40 and a protection layer 41 applied on the rod 40 except for end surfaces 40a and 40b. On the end surface 40a is fixed antibody 42 which is specifically reactive with antigen 43 contained in a sample to be analyzed.

At first a sample containing antigen to be analyzed is delivered into a reaction vessel 46 and a tip of the light guide member G is immersed into the sample to effect the antigen-antibody reaction. Then a reagent having antibody 44 labeled or coupled with pigment 45 is introduced into the reaction vessel 46 after the sample has been removed from the reaction vessel 46. In this manner, a second antigen-antibody reaction is effected to couple the antibody 44 of the reagent with the sample antigen 43 as illustrated in FIG. 7. Then an amount of the pigment 45 bound onto the end surface 40a of the rod 40 is photoelectrically detected by means of the light source 47 and light receiving element 48 after the vessel 46 is filled with a water. That is to say, light emitted from the light source 47 and transmitted through a filter F is introduced in the rod 40 via its end surface 40b and is conducted within the rod. Light transmitted through the end surface 40a is received by the light receiving element 48. This light is absorbed by the pigment 45 bound on the end surface 40a of the rod 40.

Figure 8:
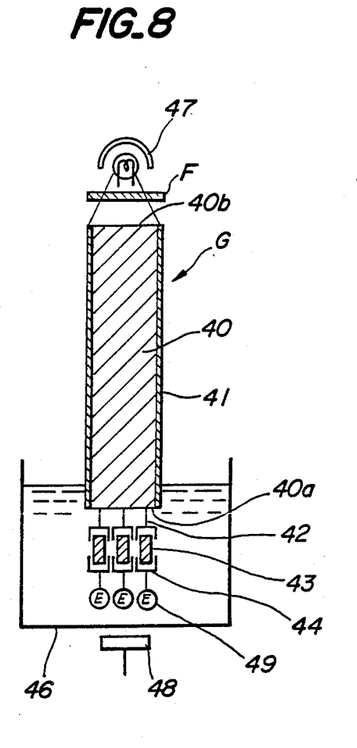

FIG. 8 is a schematic view showing a modified embodiment of the method shown in FIG. 7. In this embodiment portions similar to those shown in FIG. 7 are denoted by the same reference numerals as those used in FIG. 7. In the present embodiment use is made of a reagent comprising antibody 43 labeled with enzyme 49 instead of pigment 45. After the enzyme 49 has been bound on the end surface 40a of the light guide rod 40, the vessel 46 is filled with a color reagent including enzyme substrate to effect an enzyme reaction. A color of the enzyme reaction liquid is photometered to detect an enzyme activity which is measure of an amount of antigen 43 contained in a sample. In this manner, according to the invention an amount of substance which could not be directly measured can be detected by using suitable reagents.

Figure 9:
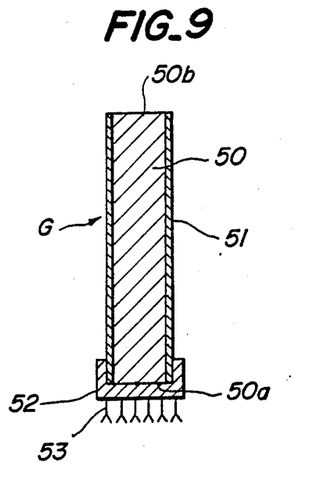
FIGS. 9 and 10 are cross-sectional views illustrating two embodiments of the light guide member according to the invention which can be repeatedly used.

FIG. 9 is a cross-sectional view depicting another embodiment of the light guide member according to the invention. In this embodiment, the light guide member G comprises a light guide rod 50 and a protection layer 51 applied on the rod except for its end surfaces 50a and 50b. Into the end portion of the rod is detachably clamped a cap-like member 52 made of transparent plastics such as polypropylene, polycarbonate and styrol, and an outer surface of the cap-like member 52 is fixed antibody 53 which is specifically reactive with antigen contained in a sample. After the measurement, the cap-like member 52 is removed from the light guide member G and a new cap-like member is clamped into the end portion of the light guide member. When there are prepared a number of cap-like members having different antibodies fixed thereto, various kinds of items can be tested, while the light guide member G is repeatedly used.

Figure 10:
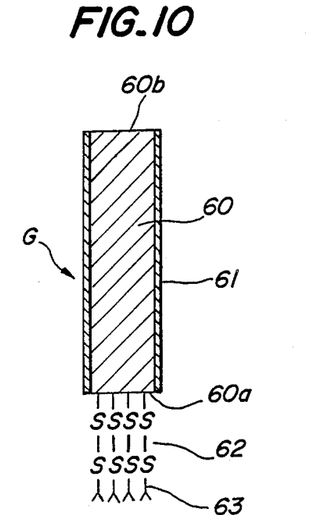

FIG. 10 is a cross-sectional view illustrating another embodiment of the light guide member according to the invention. In the present embodiment, the light guide member G comprises a light guide rod 60 and a protection layer 61 applied on the rod except for both end surfaces 60a and 60b. On the end surface 60a there is fixed S—S bond 62 and antibody or antigen 63 which is bound with the S—S bond 62, the antibody or antigen 63 being specifically reactive with antigen or antibody contained in a sample to be analyzed. After the measurement by binding the sample antigen or antibody with the antibody or antigen 63, the S—S bond 62 is cut and then new S—S bond is formed. In this manner, the light guide member G can be used repeatedly. When the cap-like member 52 and S—S bond 62 are not used, the end portion of the light guide member is cut off and antibody or antigen may be bound again.

As explained above according to the present invention, antigen or antibody contained in a sample is bound with antibody or antigen fixed onto the end surface of the light guide member and the condition of the end surface of the light guide member is photoelectrically detected. Therefore, an amount of the sample antigen or antibody can be measured simply and accurately.

The present invention further provide the method of determining the blood type of ABO system.

Figure 11:
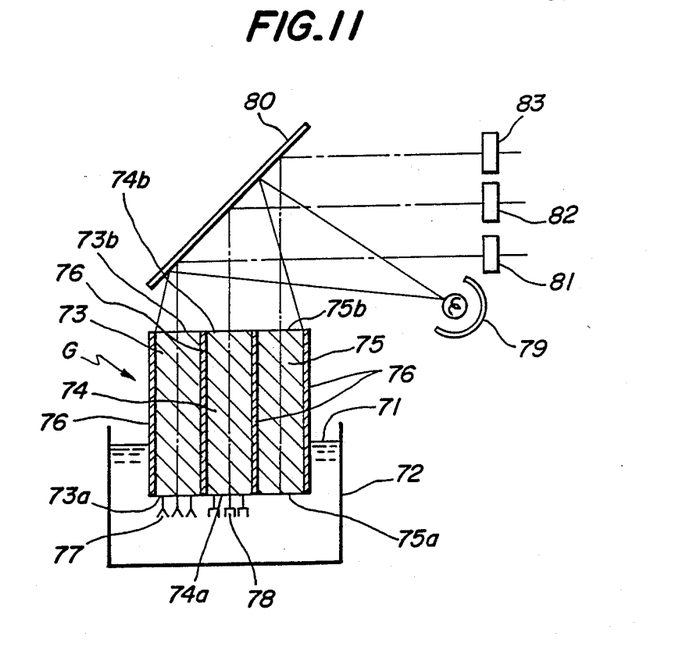
FIG. 11 is a schematic view showing an embodiment of the blood type determining apparatus according to the invention.

FIG. 11 is a schematic view showing an embodiment of the blood type determining method according to the invention. A blood sample 71 is contained in a reaction vessel 72 and an end portion of a light guide member G is immersed into the blood sample 71. The light guide member G comprises first, second and third light guide rods 73, 74 and 75 which are covered with protection layer 76 made of light shielding material. On an end surface 73a of the rod 73 there is fixed A-type antibody 77 which is specifically reactive with A-type blood cell contained in a blood sample. On an end surface 74a of the rod 74 is fixed B-type antibody which is specifically reactive with B-type blood cell in a sample. The third rod 75 serves as a reference light guide rod and to end surface 75a of this rod 75 is not fixed anything. The other end surfaces 73b, 74b and 75b of the rods 73, 74 and 75 are also not fixed with anything. There are further arranged a light source 79, a reflection mirror 80 and first, second and third light receiving elements 81, 82 and 83.

A light flux emitted from the light source 79 is reflected by the mirror 80 and is made incident upon the end surfaces 73b, 74b and 75b of the rods 73, 74 and 75. Light rays are then transmission through the rods 73, 74 and 75 up to the end surfaces 73a, 74a and 75a of the rods 73, 74 and 75. On the end surfaces 73a and 74a there are selectively bound blood cells in accordance with the blood type of a sample. When blood cells are bound on the end surface 73a or 74a, light rays are reflected by the blood cells and are made incident upon the light receiving elements 81 or 82. On the end surface 75a of the rod 75 there is not fixed any antibody, so that no blood cells are not bound thereon and almost all light rays are transmitted through the end surface 75a. Therefore, by comparing output signals from the light receiving elements 81 and 82 with an output signal from the light receiving element 83, it is possible to detect A-type blood cells or B-type blood cells bound on the end surface 73a or 74a of the rod 73 or 74.

Figure 12:
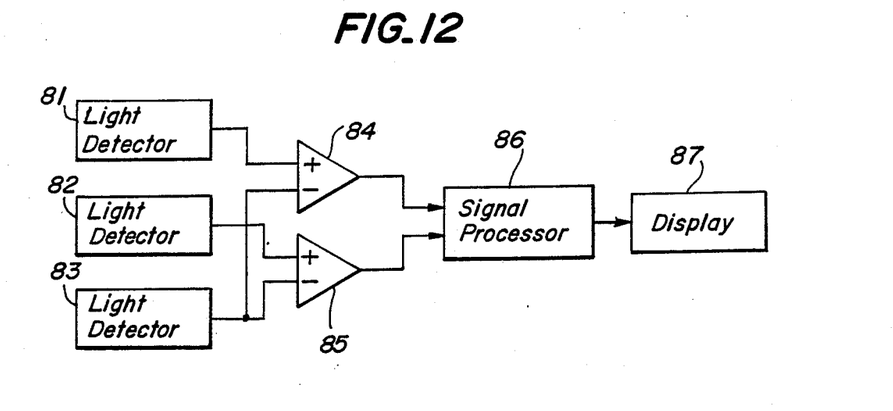
FIG. 12 is a block diagram depicting a signal processing circuit of the blood type determining apparatus.

FIG. 12 is a circuit diagram showing an embodiment of a blood type determining circuit according to the invention. Output signals from the light receiving elements 81 and 83 are supplied to a first differential amplifier 84, and output signals from the light receiving elements 82 and 83 are supplied to a second differential amplifier 85. Then, an output signal from the first differential amplifier 84 represents whether or not the A-type blood cells are bound on the end surface 73a of the first light guide rod 73, and similarly an output signal from the second differential amplifier 85 denotes whether or not the B-type blood cells are bound on the end surface 74a of the light guide rod 74. These output signals are supplied to a signal processing circuit 86 which determines the blood type of the sample in accordance with the following table.

TABLE

| Bond on first light guide | Bond on second light guide | Blood type |
| --- | --- | --- |
| + | − | A |
| + | + | AB |
| − | + | B |
| − | − | O |

Note:
+ represents that blood cells are bound on end surfaces of first and second light guide rods, and − denotes that no blood cells are bound on end surfaces.

A determined result in the signal processing circuit 86 is displayed by an output device 87 such as printer and monitor.

In the manner mentioned above according to the invention it is possible to determine the blood type of the blood sample in a simple and accurate manner.

Figure 13:
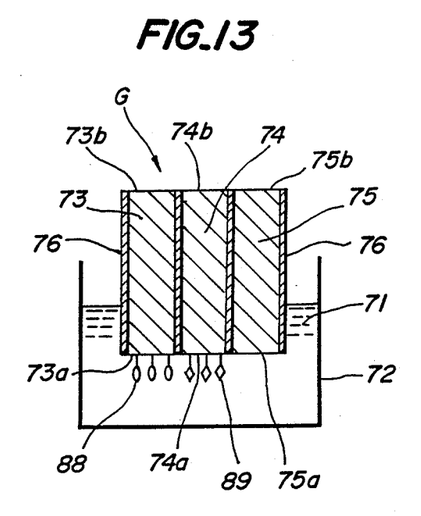
FIG. 13 is a schematic cross-sectional view illustrating another embodiment of the light guide member of the blood type determining apparatus according to the invention for effecting the indirect determination.

FIG. 13 is a cross-sectional view showing another embodiment of the light guide member according to the invention. In the embodiment shown in FIG. 12, the blood cells contained in the blood sample are detected. This detection method is usually termed as the direct detection method. In the present embodiment a so-called indirect detection method is performed. To this end, on the end surface 73a of the light guide rod 73 is fixed A-type antigen 88 which is specifically reactive with A-type antibody contained in a blood sample, and on the end surface 74a of the light guide rod 74 is fixed B-type antigen 89 which is specifically reactive with B-type antibody contained in a sample. The end portion of the light guide member G is immersed into a blood sample to effect the antigen-antibody reaction. If the sample contains A-type antibody, it is bound on the A-type antigen 88 on the end surface 73a of the rod 73, while when the sample does not contain the A-type antibody, but contains the B-type antibody, it is bound with the B-type antigen 89 fixed on the end surface 74a of the rod 74. When the antibody in the sample is bound on the end surface, it becomes opaque, so that the optical condition of the end surfaces 73a and 74a of the rods 73 and 74 can be detected photoelectrically in a similar manner to that illustrated in FIG. 11. In this manner existence of the A-type antibody and/or B-type antibody in the sample can be detected.

Figure 14:
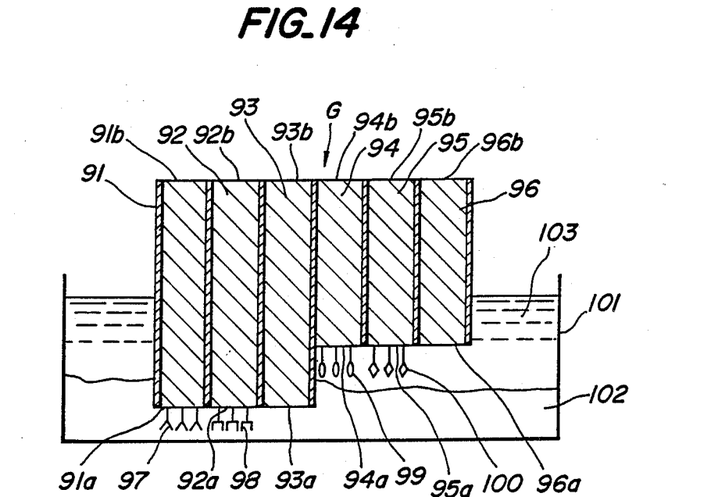
FIG. 14 is a cross-sectional view showing still another embodiment of the light guide member of the blood type determining apparatus according to the invention which effects both direct and indirect determination.

FIG. 14 is a schematic view depicting another embodiment of the light guide member G according to the invention. In the present embodiment, the direct detection method and indirect detection method are simultaneously effected so that the accuracy and reliability of the blood type determination can be further increased. The light guide member G in the present embodiment comprises six light guide rods 91 to 96. End surfaces 91a, 92a and 93a of the rods 91, 92 and 93 are made in the same level and end surfaces 94a, 95a and 96a of the rods 94, 95 and 96 are also made in the same level which situates higher than the level of the end surfaces 91a, 92a and 93a. The other end surfaces 91b to 96b of the rods 91 to 96 are made all in the same level. On the end surface 91a of the rod 91 is fixed A-type antibody 97 which is specifically reactive with A-type blood cells in a sample, and on the end surface 92a of the rod 92 is fixed B-type antibody 98 which is specifically reactive with the B-type blood cells in a sample. Further, on the end surface 94a of the rod 94 is fixed A-type antigen 99 which is selectively reactive with the A-type antibody contained in a sample, and on the end surface 95a of the rod 95 is fixed B-type antigen 100 which is specifically reactive with the B-type antibody contained in a sample. On the end surfaces 93a and 96a of the rods 93 and 96 are fixed no antibody and antigen. Therefore, these rods 93 and 96 function as the reference light guide rod.

In the present embodiment, a blood sample is poured into a reaction vessel 101 and then the reaction vessel 101 remains still or centrifuged to separate the blood sample into a clot 102 and a plasma 103. The end surfaces 91a to 93a of the rods 91 to 93 are immersed into the clot 102, but the end surfaces 94a to 96a of the rods 94 to 96 are immersed into the plasma 103. Therefore, blood cells contained in the clot 103 bound on the end surfaces 91a and/or 91b or not bound on these surfaces and antigen substances contained in the plasma 103 are bound on the end surfaces 94a and/or 95a or not bound on these surfaces. Then, the optical condition of these end surfaces 91a, 92a and 94a, 95a are photoelectrically measured while the rods 93 and 96 are used as the reference channels, respectively to effect the direct detection and indirect detection of the blood type, respectively. In the present embodiment, it is not always necessary to separate the blood sample into the clot and plasma, but the light guide member G may be immersed into the whole blood sample. In such a case it is no more necessary to make different the levels of the end surfaces 91a to 93a and 94a to 96a.

Figure 15:
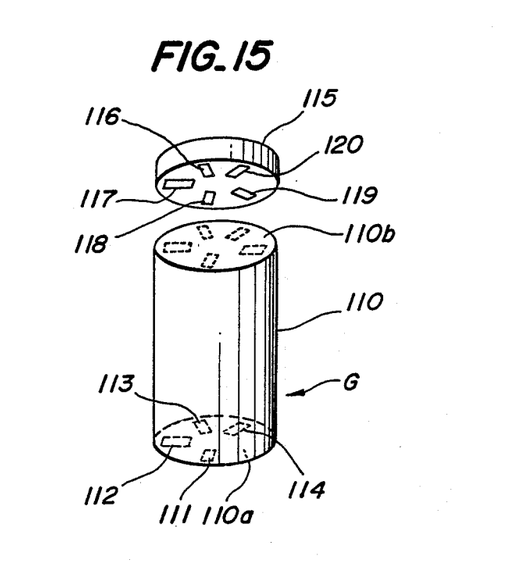
FIG. 15 is a perspective view showing still another embodiment of the blood type determining apparatus according to the invention.

FIG. 15 is a perspective view showing still another embodiment of the light guide member G according to the invention. In the present embodiment, the light guide member G comprises a single rod lens 110. On an end surface 110a of the rod lens 110 are locally fixed A-type antibody 111, B-type antibody 112, A-type antigen 113 and B-type antigen 114. On the other end surface 110b of the rod lens 110 is arranged a pick-up block 115 on which five image sensors 116 to 120 are arranged. The image sensors 116 to 120 may be formed by CCD, static induction transistor array or photodiode array. The pick-up block 115 is placed on the end surface 110b of the rod lens 110 at such a position that the image sensors 116 to 119 can pick-up images of the antibody and antigen 111 to 114, respectively formed on the end surface 110b by means of the rod lens 110, and the image sensor 120 can pick-up an image of a portion of the end surface 110a on which no antibody and antigen are fixed. Then the image sensor 120 can serve as the reference channel. By suitably processing output video signals from the image sensors 116 to 120 it is possible to effect the direct and indirect detection methods of the blood type simultaneously.

What is claimed is:

1. A method of quantifying antigen or antibody contained in a sample comprising the steps of:
   introducing a first end surface of at least one measuring light guide member and a second end surface of at least one reference light guide member into a sample, each of said measuring and reference light guide members being coated with a protection layer except for said first and second end surfaces and an other end surface of respective light guides, and only on said first end surface of the measuring light guide member being fixed a substance which is specifically reactive with a substance in the sample to be analyzed, whereby an antigen-antibody reaction is effected between the substance fixed on the measuring light guide member and the substance in the sample;
   photoelectrically detecting optical properties of said first and second end surfaces of the measuring and reference light guide members, respectively, by transmitting light through the measuring and reference light guide members to derive detection signals; and
   measuring the antigen or antibody in the sample by processing said detection signals.

2. A method according to claim 1, wherein said step of photoelectrically detecting optical properties of the first and second end surfaces of the light guide members further comprises introducing light into each light guide member from the other end surfaces thereof and photoelectrically detecting light emanating from the first and second end surfaces of the light guide members.

3. A method according to claim 2, wherein the light emanating from the first and second end surfaces of the light guide members is detected while each of said first and second end surfaces is immersed in a liquid.

4. A method according to claim 3, wherein the liquid is composed of clear water and said first end surface of the at least one measuring light guide member is washed in said clear water.

5. A method according to claim 2, wherein the light emanating from the first and second end surfaces of the light guide members is detected while said first and second end surfaces are positioned in the air.

6. A method according to claim 2, wherein the light is introduced into the light guide members at said other end surfaces thereof via a color filter whose transmission wavelength corresponds to an absorption wavelength of the substance contained in the sample.

7. A method according to claim 1, wherein said optical property of each of the first and second end surfaces of the light guide members is photoelectrically detected by introducing light into the light guide members at said first and second end surfaces of each member and by detecting light emanating from an other end surface of each light guide member.

8. A method according to claim 7, wherein the light is introduced into each light guide member at said first and second end surfaces of the members via a liquid.

9. A method according to claim 8, wherein said liquid is composed of clear water and said first end surface of the measuring light guide member is washed in the clear water.

10. A method according to claim 8, wherein the liquid is contained in a vessel having a reflective spherical bottom surface and the light reflected by the spherical bottom surface is collected at the first and second end surfaces of the light guide members.

11. A method according to claim 1, wherein said optical property of said first and second end surfaces of the light guide members is photoelectrically detected by introducing light into the light guide members from the other end surfaces thereof and by detecting light which is transmitted through the first and second end surfaces of the light guide members, modulated by the optical property of the first and second end surfaces of the light guide members, made incident again upon the first and second end surfaces of the light guide members and emanates from the other end surface of the light guide members.

12. A method according to claim 11, wherein the optical property of the first end surface of the at least one measuring light guide member is detected by detecting light reflected by the substance in the sample bound on the first end surface of each of the measuring light guide members.

13. A method according to claim 11, wherein the optical property of the first and second end surfaces of the light guide members is detected by detecting light transmitted through the first and second end surfaces of the light guide members twice.

14. A method according to claim 13, wherein light emanating from the first and second end surfaces of the light guide members is reflected by a mirror surface arranged in opposition to the first and second end surfaces of the light guide members and is made incident upon the first and second end surfaces of the light guide members.

15. A method according to claim 14, wherein said first and second end surfaces of the light guide members are immersed in a liquid contained in a vessel and said mirror surface is formed in a bottom wall of the vessel.

16. A method according to claim 1, wherein after the light guide members are introduced into the sample the sample is replaced by a labeling reagent; said light guide members are immersed in the labeling reagent, said labeling reagent comprising a substance which is specifically reactive with the substance in the sample and is labeled with a labeling substance.

17. A method according to claim 1, wherein said labeling substance is a pigment.

18. A method according to claim 1, wherein said labeling substance is an enzyme.

19. A method according to claim 1, wherein said steps are repetitively carried out to analyze different samples and said light guide members are repeatedly used for analyzing said different samples.

20. A method according to claim 1, wherein each of said measuring light guide members comprises a light guide element and a cap-like member made of transparent material and is detachably secured to one end portion of the light guide element, onto an outer surface of the cap-like member being fixed said substance which is specifically reactive with the substance contained in the sample.

21. A method according to claim 1, wherein said substance which is specifically reactive with the substance in the sample is fixed onto the first end surface of the measuring light guide member by means of an S—S bond.

22. A method according to claim 19, wherein after a sample has been analyzed, one end portion of each of the measuring light guide members including said first end surface is removed, and replaced by a new first end portion including a new first end surface of the light guide member, onto which is fixed a new substance which is specifically reactive with a substance in a sample next to be analyzed.

23. A method according to claim 1, wherein said protection layer is made of light shielding material.

24. An apparatus for analyzing antigen or antibody contained in a sample comprising:
at least one measuring light guide member having first and an other end surfaces, said measuring light guide member being coated with a protection layer except for said first and the other end surfaces and on said first end surface of the measuring light guide member being fixed a substance which is selectively reactive with an antigen or antibody in the sample to be analyzed;
at least one reference light guide member having second and an other end surfaces, said reference light guide member being coated with a protection layer except for said second and the other end surfaces;
a light source for emitting light which is transmitted through the measuring and reference light guide members; and
a photoelectric detector for detecting light transmitted through the measuring and reference light guide members and modulated by the first and second end surfaces of the light guide members to derive detection signals representing optical 25. An apparatus according to claim 24, wherein each of said light guide members is formed by a light guide rod.

26. An apparatus according to claim 24, wherein each of said light guide members is formed by an optical fiber bundle.

27. An apparatus according to claim 24, wherein each of said light guide members is formed by an optical wave guide.

28. An apparatus according to claim 24, further comprising a vessel having a reflective bottom surface arranged in opposition to the first end surfaces of the light guide members.

29. An apparatus according to claim 28, wherein said reflective bottom surface is formed as a spherical shape.

30. An apparatus according to claim 29, wherein said light guide members are secured to the vessel such that said one end surfaces of the light guide members are positioned substantially at a center of the spherical bottom surface.

31. An apparatus according to claim 24, wherein said reference light guide member is secured to said measuring light guide member side by side.

32. An apparatus according to claim 31, wherein said optical property of the measuring light guide member is detected by deriving a difference between said detection signals.

33. An apparatus according to claim 24, wherein said protection layer is made of light shielding material.

34. An apparatus according to claim 24, wherein said measuring light guide member comprises a measuring light guide element and a cap-like member made of transparent material and detachably clamped to one end portion of the light guide element, on an outer surface of the cap-like member being fixed said substance which is specifically reactive with the substance in the sample to be analyzed.

35. An apparatus according to claim 24, wherein said substance specifically reactive with the substance in the sample to be analyzed is fixed onto the first end surface of the measuring light guide member by means of an S—S bond.

36. A method of measuring different types of substances contained in a sample, comprising the steps of:
introducing first end surfaces of at least first and second light guide members into a sample, each of said first and second light guide members being coated with a protection layer except for said first and an other end surfaces and on respective first end surfaces of the first and second light guide members being fixed different substances which are selectively and specifically reactive with different substances in the sample, whereby an antigen-antibody reaction is effected between the substances fixed on the first and second light guide members and the antigen or antibody in the sample;
detecting optical properties of the first end surfaces of the first and second light guide members to derive first and second at least two detection signals; and
processing said first and second output detection signals to measure the different types of substances in the sample.

37. A method according to claim 36, further comprising deriving a third detection signal representing an optical property of a second end surface of a reference light guide member, and deriving first and second difference signals between the first and third detection signals and between the second and third detection signals, wherein the substances in the sample are determined by processing said first and second difference signals.

38. A method according to claim 36, wherein a blood type of a blood sample is determined by a direct method in which A-type antibody and B-type antibody are fixed on the first end surfaces of the first and second light guide members, respectively.

39. A method according to claim 36, wherein a blood type of a blood sample is determined by an indirect method in which A-type antigen and B-type antigen are fixed on the first end surfaces of the first and second light guide members, respectively.

40. A method according to claim 39 wherein the blood sample is separated into clot and plasma, and said first end surfaces of the first and second light guide members are immersed into the plasma.

41. An apparatus for determining a blood type of a blood sample comprising first and second light guide members having first and an other end surfaces, each of said light guide members being coated with a protection layer except for said first and the other end surfaces and on the first end surface of the first light guide member being fixed A-type antibody or antigen and on the first end surface of the second light guide member being fixed B-type antibody or antigen;
a light source for emitting light transmitted through the first and second light guide members;
first and second light detectors for receiving light transmitted through the first and second light guide members, respectively, to derive first and second detection signals representing optical properties of the first end surfaces of the first and second light guide members; and
a signal processing circuit for determining a blood type of the blood sample in accordance with the first and second detection signals.

42. An apparatus according to claim 41, wherein said first and second light guide members are coupled with each other side by side.

43. An apparatus according to claim 41, further comprising a reference channel including a reference light guide member and a third photoelectric detector for detecting an optical condition of second end surface of the reference light guide member.

44. An apparatus according to claim 43, wherein said first and second light guide members and reference light guide member are coupled with each other such that the first and second end surfaces of these light guide members are aligned in one plane.

45. An apparatus according to claim 41, wherein said first and second light guide members are formed by a single light guide element.

46. An apparatus according to claim 45, wherein said single light guide element is formed by a rod lens.

47. An apparatus according to claim 41, further comprising third and fourth light guide members having first end surfaces on which A-type antigen or antibody and B-type antigen or antibody are fixed, respectively.

48. An apparatus according to claim 47, wherein a level of the first end surfaces of the first and second light guide members is made different from a level of the one end surfaces of the third and fourth light guide members.

49. An apparatus according to claim 48, further comprising first and second reference light guide members constituting first and second reference channels, a level of a second end surface of the first reference light guide member is made the same as a level of the first end surfaces of the first and second light guide members and a level of a second end surface of the second reference light guide member is made the same as a level of the first end surfaces of the third and fourth light guide members.

50. A method of determining a blood type of a blood sample which is separated into first and second components comprising the steps of:
introducing first end surfaces of at least first and second light guide members into said first and second components of the blood sample, respectively, each of said first and second light guide members being coated with a protection layer except for said first and an other end surfaces, and the first end surfaces of the first and second light guide members being fixed with different substances which are specifically reactive with substances in the blood sample, and said first end surfaces of the first and second light guide members being arranged into levels of the first and second components of the blood sample, respectively;
detecting optical properties of the first end surfaces of the first and second light guide members to derive first and second detection signals; and processing said first and second detection signals to determine the blood type of the blood sample.

51. A method according to claim 50, wherein said substances fixed on the first end surfaces of the first and second light guide members are the same type of antibody and antigen which are respectively reactive with antigen in the first component in the blood sample and with antibody in the second component in the blood sample.

52. A method according to claim 51, wherein blood type A or B is determined.

53. A method according to claim 52, wherein the first component is a clot and the second component is a plasma.

54. A method according to claim 52, wherein said first end surfaces of the first and second light guide members are immersed into the first and second components of the blood sample simultaneously.

55. A method according to claim 50, wherein said protection layer is made of light shielding material.

* * * * *